US012714720B2

(12) United States Patent
Avram

(10) Patent No.: US 12,714,720 B2
(45) Date of Patent: Aug. 25, 2026

(54) PAIN-RELIEVING TOPICAL COMPOSITIONS

(71) Applicant: INNOCAN PHARMA LTD., Herzliya (IL)

(72) Inventor: Nir Avram, Metar (IL)

(73) Assignee: INNOCAN PHARMA LTD., Herzliya (IL)

( * ) Notice: Subject to any disclaimer, the term of this patent is extended or adjusted under 35 U.S.C. 154(b) by 548 days.

(21) Appl. No.: 18/327,103

(22) Filed: Jun. 1, 2023

(65) Prior Publication Data

US 2023/0302028 A1 Sep. 28, 2023

Related U.S. Application Data

(63) Continuation-in-part of application No. 16/968,627, filed as application No. PCT/IL2019/050776 on Jul. 11, 2019, now Pat. No. 11,696,909.

(60) Provisional application No. 62/696,341, filed on Jul. 11, 2018.

(51) Int. Cl.

| | |
|---|---|
| ***A61K 31/00*** | (2006.01) |
| ***A61K 9/00*** | (2006.01) |
| ***A61K 9/06*** | (2006.01) |
| ***A61K 31/05*** | (2006.01) |
| ***A61K 31/216*** | (2006.01) |
| ***A61K 33/06*** | (2006.01) |

(52) U.S. Cl.

CPC .......... *A61K 31/658* (2023.05); *A61K 9/0014* (2013.01); *A61K 9/06* (2013.01); *A61K 31/05* (2013.01); *A61K 31/216* (2013.01); *A61K 33/06* (2013.01)

(58) Field of Classification Search

CPC .................................................... A61K 31/658

See application file for complete search history.

(56) References Cited

U.S. PATENT DOCUMENTS

| | | | |
|---|---|---|---|
| 6,949,582 | B1 | 9/2005 | Wallace |
| 9,717,757 | B1 | 8/2017 | Gasque, Jr. |
| 2014/0018750 | A1 | 1/2014 | Pagliaro |
| 2015/0126595 | A1 | 5/2015 | Smith |

FOREIGN PATENT DOCUMENTS

| | | |
|---|---|---|
| WO | 2010126501 | 11/2010 |

OTHER PUBLICATIONS

Dwivedi, Evergreening: A deceptive device in patent rights, Technology in Society 32 (2010) 324-330.*

Feldman, Understanding 'Evergreening' : Making Minor Modifications of Existing Medications to Extend Protections, Health Affairs Jun. 2022 41:6, 801-804.*

CBD Medic—Arthritis Deep Relief product information (total 3 pages).

Dragon Balm description (total 2 pages).

Ultra Strength Bengay Cream product information (total 7 pages).

Marinotti, Osvaldo, and Miles Sarill. "Differentiating full-spectrum hemp extracts from CBD isolates: Implications for policy, safety and science." Journal of Dietary Supplements 17.5 (2020): 517-526.

CBD vs Hemp Extract vs Hemp Seed Oil: Know What You Buy | Your Guide to Understanding CBD Oil, dated Apr. 6, 2022 (total of 4 pages) https://www.palmorganix.com/cbdvs-hemp-extract-vs-hemp-seed-oil-know-what-you-buy/.

* cited by examiner

*Primary Examiner* — Nizal S Chandrakumar
(74) *Attorney, Agent, or Firm* — JMB Davis Ben-David

(57) ABSTRACT

Described herein are compositions for topical use comprising active agents to provide pain relief. The compositions comprise a magnesium salt, a cannabinoid and at least one additional topical analgesic agent. Additionally described herein are methods for treating pain comprising administering to a person in need thereof a composition comprising a pharmaceutically effective amount of a cannabinoid, a magnesium salt and at least one of: methyl salicylate, and menthol.

8 Claims, No Drawings

PAIN-RELIEVING TOPICAL COMPOSITIONS

CROSS-REFERENCE TO RELATED APPLICATIONS

This is a Continuation-In-Part of U.S. application Ser. No. 16/968,627 which is the US National Stage of International Patent Application No. PCT/IL 2019/050776, filed on Jul. 11, 2019, which in turn claims the benefit to U.S. Provisional Patent Application No. 62/696,341 filed Jul. 11, 2018. The contents of the foregoing patent applications are incorporated by reference herein in their entirety.

FIELD

Provided herein are topical compositions for the alleviation of pain.

BACKGROUND

Pain is an unpleasant sensory and emotional experience associated with tissue damage. Pain is typically a symptom of an underlying disease or condition.

Pain may be treated through various methods. One of the methods of pain treatment is administration of an analgesic, a drug administered to alleviate pain in a subject. There are a number of groups of analgesic having various mechanisms of action. Some of these groups include opioids, COX-2 inhibitors, and other COX inhibitors, also known as non-steroidal anti-inflammatory drugs (NSAID).

An analgesic may be administered systemically, for example orally, in the form of a tablet or a syrup, or parenterally, in the form of an injection. Alternatively, analgesics may be administered topically, in the form of a cream, ointment, paste, gel, suspension, pump spray, aerosol spray, aerosol foam, liquid, powder, stick, or lotion. Some analgesics such as COX-2 inhibitors have been associated with side effects such as cardiovascular events and gastrointestinal bleeding. Topical administration of analgesics may be advantageous in limiting systemic exposure to analgesics, thereby reducing potential for side effects.

SUMMARY

Described herein are compositions for topical use comprising active agents to provide pain relief. The compositions comprise a magnesium salt, a cannabinoid and at least one additional topical analgesic agent.

Additionally described herein are methods for treating pain comprising administering to a person in need thereof a composition comprising a pharmaceutically effective amount of a cannabinoid, a magnesium salt and at least one of: methyl salicylate, and menthol.

Additionally described herein are methods for treating pain comprising administering to a person in need thereof such compositions are described herein.

The foregoing and other objects, features, and advantages will become more apparent from the following detailed description.

DETAILED DESCRIPTION

Unless otherwise noted, technical terms are used according to conventional usage. Definitions of common terms in pharmaceutical sciences can be found in Troy et al. *Remington: The Science and Practice of Pharmacy*. Published by Lippincott Williams & Wilkins, 2006. In case of conflict, the present specification, including explanations of terms, will control. In addition, all the materials, methods, and examples are illustrative and not intended to be limiting.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia and is used herein to indicate a non-limiting example. Thus, the abbreviation "e.g." is synonymous with the term "for example."

As mentioned above, embodiments relate to compositions comprise methyl salicylate, menthol, a magnesium salt and a cannabinoid. Without being bound by theory, it is suggested that cannabinoids will act synergistically with a magnesium salt and with the pain-relieving ingredient (methyl salicylate and/or others) to provide a pain relieving, soothing effect.

Methyl salicylate is the methyl ester of salicylic acid. It is produced by some plants and is known as wintergreen oil. Methyl salicylate is a commercially available compound and has been used topically to treat muscular pain and joint pain.

According to an embodiment, methyl salicylate may be present in an amount between about 0.1% and about 30% of the composition. Optionally, methyl salicylate may be present in an amount between about 10% and about 20% of the composition. Optionally, methyl salicylate may be present in an amount about 10% of the composition Optionally, methyl salicylate may be present in an amount about 15% of the composition.

Menthol is an organic, naturally occurring substance found in wild mint. It can be administered topically to provide a cooling, analgesic sensation when applied.

According to an embodiment, menthol may be present in an amount between about 0.1% and about 15% of the composition. Optionally, menthol may be present in an amount between about 2% and about 15% of the composition. Optionally, menthol may be present in an amount of about 10% of the composition. Optionally, menthol may be present in an amount of about 2% of the composition.

Magnesium salts are salts comprising magnesium as a cation. Magnesium salts, particularly magnesium chloride, have been used in topical applications to humans. Optionally, the magnesium salt is magnesium chloride, magnesium sulfate, magnesium bromide, magnesium carbonate, magnesium bicarbonate, magnesium hydroxide, magnesium L-pyrrolidone carboxylic acid (Mg-PCA), and magnesium oxide. Preferably the magnesium salt is magnesium sulfate or magnesium chloride. Most preferably the magnesium salt is magnesium chloride ($MgCl_2$). A hydrate of a magnesium salt may be used, for example, magnesium chloride hexahydrate. The amount of magnesium ion in the composition may be between about 0.25% to about 10% by weight of the composition, preferably between about 1% and about 6% of the composition. The amount of magnesium ion may be between about 4% and 6% of the composition.

A cannabinoid is a chemical compound that acts on cannabinoid receptors in cells in mammals, including in humans. Cannabinoids can be manufactured synthetically or obtained from various parts of the genus Cannabis, in particular, from the species Cannabis Sativa. Two preferred cannabinoids according to various embodiments, are (−)-trans-$\Delta^9$-tetrahydrocannabinol, and/or isomers thereof (THC) and cannabidiol (CBD). Alternatively, a cannabinoid may be in the form of hemp oil. Alternatively, a cannabinoid may be in the form of cannabis oil. Compositions described herein may comprise one cannabinoid or multiple cannabinoids, such as a combination of CBD and THC.

According to an embodiment, a cannabinoid may be present in an amount between about 0.1% and about 10% of the composition. Optionally, a cannabinoid may be present in an amount between about 0.1% and 1% of the composition. Optionally, the cannabinoid may be present in an amount between 0.45% and 0.55% of the composition, preferably 0.5% of the composition.

Optionally, the composition may further comprise camphor. The camphor may be present in an amount between about 0.1% and about 10% of the composition, optionally between about 2% and about 5% of the composition, optionally about 4% of the composition.

According to an embodiment, the composition may comprise a magnesium salt, a cannabinoid and at least one additional topical analgesic agent. The at least one additional topical analgesic agent may be selected from the group consisting of: alcohol, ethoxylated alkyl alcohol, allantoin, allyl isothiocyanate, aluminum acetate, aluminum chloride hexahydrate, aluminum hydroxide, ammonia solution, aspirin, benzalkonium chloride, benzethonium chloride, benzocaine, benzyl alcohol, bismuth sodium tartrate, bithionol, butamben picrate, calamine, camphor, camphorated metacresol, capsaicin, capsicum, capsicum oleoresin, cetalkonium chloride, chloral hydrate, chlorobutanol, chlorpheniramine maleate, creosote, cupric sulfate, cyclomethycaine sulfate, dexpanthenol, dibucaine, dimethisoquin hydrochloride, diperodon hydrochloride, diphenhydramine hydrochloride, dyclonine hydrochloride, ephedrine hydrochloride, ergot fluid extract, eucalyptus oil, eugenol, ferric chloride, glycerin, glycol salicylate, hectorite, hexylresorcinol, histamine dihydrochloride, hydrocortisone, hydrocortisone acetate, hydrogen peroxide, impatiens biflora tincture, iron oxide, isopropyl alcohol, juniper tar, lanolin, lidocaine, menthol, merbromin, methapyrilene hydrochloride, methyl nicotinate, methyl salicylate, panthenol, parethoxycaine hydrochloride, pectin, peppermint oil, phenol, phenolate sodium, phenyltoloxamine dihydrogen citrate, povidone-vinylacetate copolymers, pramoxine hydrochloride, pyrilamine maleate, resorcinol, salicylamide, simethicone, sodium bicarbonate, sodium borate, sulfur, tannic acid, tetracaine, thymol, topical starch, tripelennamine hydrochloride, trolamine, trolamine salicylate (trietnanolamine salicylate), turpentine oil, zinc acetate, zinc oxide, zinc sulfate, zirconium oxide and zyloxin.

According to an embodiment, the composition may be in the form of a cream, ointment, paste, gel, suspension, pump spray, aerosol spray, non-pressurized spray, continuous spray, non-chlorofluorocarbon-based spray, aerosol foam, liquid, solution, powder, stick, roll-on or lotion.

In addition to active ingredients, compositions described herein may further comprise at least one inert ingredient. The inert ingredient may be selected from the group consisting of: water, a solvent, an emulsifier, an emollient, a moisturizer, a pH adjustment agent, a polymer, a humectant, an occlusive agent, a preservative, a thickener, an anti-irritation agent, a conditioning agent, a buffer, a vitamin, an extract, a natural oil, a wax, a penetration enhancer, a peptide, a sugar derivative, a fatty acid, a fatty alcohol, a silicone, a polyethyl-glycol, a fragrance, a pigment, an ester, a triglyceride, a butter, hyaluronic acid, and an absorbing powder.

The preservative may be selected from the group consisting of: a parahydroxybenzoic acid, methylparaben, propylparaben, Benzyl Alcohol, Phenoxyethanol, Ethylhexylglycerin, Octanediol, Hexanediol, Pentandiol, Sorbitan Caprylate, capralyl glycol, caprylhydroxamic acid, Phenoxyethanol Triethylene glycol, sodium benzoate, and Bronopol.

As described herein, certain embodiments relate to methods for treatment of pain comprising administering to a patient in need thereof a composition comprising a pharmaceutically effective amount of methyl salicylate, menthol, a magnesium salt and a cannabinoid. According to an embodiment, the methods relieve pain, provide muscle relief, provide topical anesthesia, provide topical analgesia or have an antipruritic effect. Optionally the compositions may be used for temporary relief of pain and/or itching associated with minor burns, sunburn, minor cuts, scrapes, insect bites or minor skin irritations and for temporary protection from minor skin irritation. Optionally, the compositions may be used for alleviating joint pain. Optionally, the compositions may be used for alleviating pain associated with backache, arthritis, strains, bruises, back pain, neck pain, knee pain, foot pain, or sprains.

According to an embodiment, the composition may be applied between once and 4 times daily.

According to an embodiment, the composition may be applied in a dosage of between about 0.1 milliliter (ml) and about 10.0 ml per application.

According to an embodiment, the composition is a cream for topical administration. According to an embodiment, the composition is a biphasic composition, adapted for packaging in a spray bottle. Optionally, the spray bottle is configured to be shaken before use, to combine both phases of the composition.

The following examples are provided to illustrate certain particular features and/or embodiments. These examples should not be construed to limit the disclosure to the particular features or embodiments described.

EXAMPLES

Example 1A: Attempts to Prepare Oil in Water Cream Compositions

A composition is prepared using the ingredients listed in Table 1:

TABLE 1

| Ingredient | Function | Amount (weight percent) |
|---|---|---|
| Water | Aqueous solvent | 49.6 |
| Glycerin 99.7% | Humectant | 4.0 |
| Magnesium PCA | Pain relief/ muscle relaxation | 0.4 |
| Glyceryl stearate | Emulsifier | 3.5 |
| Stearic Acid | Emulsifier/thickener | 1.5 |
| Cetyl Alcohol | Thickener | 3.0 |
| Stearyl Alcohol | Thickener | 3.0 |
| Isopropyl alcohol | Solvent | 3.0 |
| Potassium cetyl phosphate | Emulsifier | 1.0 |
| Euxyl PE 9010 | Preservative | 1.0 |

TABLE 1-continued

| Ingredient | Function | Amount (weight percent) |
|---|---|---|
| (Phenoxyethanol and ethylhexylglycerin) | | |
| Hemp oil, 10% CBD | Pain relief | 5.0 |
| Methyl salicylate | Pain relief | 15.0 |
| Menthol | Cooling and pain relief | 10.0 |
| Total | | 100 |

Water is added to glycerin and heated to 65° C. Magnesium is added, and the mixture is mixed. In a separate vessel the oil phase is prepared using glyceryl stearate, stearic acid, cetyl alcohol, stearyl alcohol, isopropyl alcohol, potassium cetyl phosphate, Euxyl PE 9010 and hemp oil, which are heated to 65° C. and mixed until all solids and waxes are dissolved. The water phase and oil phase are combined and homogenized for 15 minutes. Homogenizing is stopped, and the mixture is cooled while mixing. At a temperature of 55° C., the active ingredients methyl salicylate and menthol are added and homogenized for 2 minutes. Cooling is then continued while gently mixing to a temperature of 35° C. The pH is measured then adjusted with triethanolamine or lactic acid to achieve a pH of 5.0-6.5.

The viscosity is measured to be between 10,000-40,000 centipoise (cps). The amount of CBD in the composition is between 0.45-0.55%. The amount of menthol in the composition is between 9.0-11.0%. The amount of methyl salicylate in the composition is between 13.5 and 16.5%.

The compositions prepared lacked stability, and the emulsion was broken, causing phase separation within two months of preparation.

Example 1B: Additional Attempts to Prepare Oil in Water Emulsions in Cream Form

A composition is prepared using the ingredients listed in Table 2:

TABLE 2

| Ingredient | Function | Amount (weight percent) |
|---|---|---|
| Water | Aqueous solvent | 52.6 |
| Glycerin 99.7% | Humectant | 3.0 |
| Magnesium Aluminum Silicate | Pain relief/ muscle relaxation | 1.00 |
| Polysorbate 80 | Emulsifier/solubilizer | 0.50 |
| Arlacel 165 (glycerol monostearate + PEG-100 Stearate) | Emulsifier (oil in water) | 3.50 |
| Stearic Acid | Emulsifier/thickener | 1.5 |
| Cetyl Alcohol | Thickener | 2.5 |
| Stearyl Alcohol | Thickener | 3.0 |
| Hemp oil, 10% CBD | Pain relief | 5.0 |
| Potassium cetyl phosphate | Emulsifier | 1.0 |
| Euxyl PE 9010 (Phenoxyethanol and ethylhexylglycerin) | Preservative | 1.0 |
| Methyl salicylate | Pain relief | 15.0 |
| Menthol | Cooling and pain relief | 10.0 |
| Magnesium PCA | Pain relief | 0.4 |
| Total | | 100 |

Water is added to glycerin and magnesium aluminum silicate and is heated to 75° C. and homogenized to form a homogenous gel. In a separate vessel the oil phase is prepared using Polysorbate 80, arlacel, stearic acid, cetyl alcohol, stearyl alcohol, hemp oil, potassium cetyl phosphate, and Euxyl PE 9010, which are heated to 65° C. and mixed until all solids and waxes are dissolved. The water phase and oil phase are combined and homogenized for 15 minutes. Homogenizing is stopped, and the mixture is cooled while mixing. At a temperature of 55° C., the active ingredients methyl salicylate and menthol are added and homogenized for 2 minutes. Cooling is then continued while gently mixing to a temperature of 35° C. The pH is measured then adjusted with triethanolamine or lactic acid to achieve a pH of 5.0-6.5.

The viscosity is measured to be between 15,000 and 30,000 cps. The amount of CBD in the composition is between 0.45-0.55%. The amount of menthol in the composition is between 9.0-11.0%. The amount of methyl salicylate in the composition is between 13.5 and 16.5%.

The compositions prepared lacked stability, and the emulsion was broken, causing phase separation within less than one week from preparation.

Attempts to prepare compositions having high concentrations of magnesium salts, which are water soluble, with additional active ingredients, such as cannabinoids, in oil in water emulsions, were not successful in preparing stable creams. Additional attempts to prepare oil in water emulsions were unsuccessful using various concentrations of magnesium salts and alternate emulsifiers.

Example 2A: Preparation of Water in Oil Emulsion

A composition is prepared using the ingredients listed in Table 3:

TABLE 3

| Ingredient | Function | Amount (weight percent) |
|---|---|---|
| Water | Aqueous solvent | 37.3 |
| Magnesium Chloride | Pain relief/ muscle relaxation | 10.0 |
| Propylene Glycol | Solvent | 10.0 |
| Alcohol (absolute) | Solvent | 10.0 |
| Menthol | Pain Relief | 10.0 |
| SF1540 (Cyclopentasiloxane and PEG/PPG-20/15 dimethicone) | Emulsifier | 3.0 |
| Hemp oil (10% CBD) | Pain Relief | 5.0 |
| Cyclopentasiloxane | Lubricant | 14.7 |

The SF1540 is combined with hemp oil and cyclopentasiloxane until a homogenous liquid is obtained. In a separate container, magnesium chloride is dissolved in water. In another separate vessel menthol is dissolved in alcohol and propylene glycol. The water phase and the propylene glycol phases are combined until a clear solution is obtained. While mixing the hemp oil containing phase, the clear aqueous/propylene glycol solution is added slowly. After combining, the phases are mixed vigorously for 5 minutes, then homogenized at high speed for 5 minutes until a stable emulsion is formed.

The pH is measured then adjusted with triethanolamine or lactic acid to achieve a pH of 5.0-6.5.

The viscosity is measured to be between 2,000 and 6,000 cps. The amount of CBD in the composition is between 0.45-0.55%. The amount of menthol in the composition is between 9.0-11.0%.

Example 2B: Additional Cream Compositions, Water in Oil Emulsion

A composition is prepared using the ingredients listed in Table 4:

TABLE 4

| Ingredient | Function | Amount (weight percent) |
|---|---|---|
| Water | Aqueous solvent | 37.0 |
| Magnesium Chloride | Pain relief/ muscle relaxation | 10.0 |
| Propylene Glycol | Solvent | 10.0 |
| Alcohol (absolute) | Solvent | 10.0 |
| Menthol | Pain Relief | 10.0 |
| SF1540 (Cyclopentasiloxane and PEG/PPG-20/15 dimethicone) | Emulsifier | 3.0 |
| Hemp oil (10% CBD) | Pain Relief | 5.0 |
| Methyl Salicylate | Pain Relief | 15.0 |

The SF1540 is combined with hemp oil and methyl salicylate until a homogenous liquid is obtained. In a separate container, magnesium chloride is dissolved in water. In another separate container menthol is dissolved in alcohol and propylene glycol. The water phase and the propylene glycol phases are combined until a clear solution is obtained. While mixing the hemp oil containing phase, the clear aqueous/propylene glycol solution is added slowly. After combining, the phases are mixed vigorously for 5 minutes, then homogenized at high speed for 5 minutes until a stable emulsion is formed.

The pH is measured then adjusted with triethanolamine or lactic acid to achieve a pH of 5.0-6.5.

The viscosity is measured to be between 2,000 and 6,000 cps. The amount of CBD in the composition is between 0.45-0.55%. The amount of menthol in the composition is between 9.0-11.0%. The amount of methyl salicylate in the composition is between 13.5 and 16.5%.

The water in oil compositions prepared in examples 2A and 2B were stable, despite relatively high magnesium concentrations. They maintained stability of the emulsion even at a relative humidity of 75% and temperature of 40° C. for three months.

Water in oil compositions such as those described in the above examples may be packaged in a roll-on container for easy application to the skin of a patient in need thereof.

In addition to emulsifiers described in examples 2A and 2B, other emulsifiers which may be used include: Dow Corning® 5225C, comprising 12.5% dispersion of high molecular weight silicone polyether in decamethylcyclopentasiloxane; ABIL® EM 90 (Cetyl PEG/PPG-10/1 Dimethicone); and Dow Corning® ES-5300, Lauryl PEG-10 Tris (trimethylsiloxy) silylethyl Dimethicone.

Example 3A

Compositions for Topical Administration

Spray on composition, configured to be introduced into a pump-spray bottle, shaken, and then sprayed on, is prepared using the ingredients listed in Table 5.

TABLE 5

| Ingredient | Function | Amount (weight percent) |
|---|---|---|
| Water | Aqueous solvent | 37.0 |
| Magnesium Chloride Hexahydrate | Pain relief/ muscle relaxation | 34.0 |
| Menthol | Pain Relief | 2.0 |
| Methyl Salicylate | Pain Relief | 10.0 |
| Denatured Ethanol SD#40 | Solvent | 10.0 |
| Polysorbate-20 (Tween-20) | Emulsifier | 2.0 |
| Hemp oil, 10% CBD | Pain Relief | 5.0 |

Water is added to magnesium chloride salt and mixed to form a clear solution. In a separate container, menthol, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing and homogenizing. A white lotion is formed.

Example 3B

Compositions for Topical Administration

Spray on composition, configured to be introduced into a pump-spray bottle, shaken, and then sprayed on, is prepared using the ingredients listed in Table 6.

TABLE 6

| Ingredient | Function | Amount (weight percent) |
|---|---|---|
| Water | Aqueous solvent | 34.0 |
| Magnesium Chloride Hexahydrate | Pain relief/ muscle relaxation | 34.0 |
| Menthol | Pain Relief | 5.0 |
| Propylene Glycol | Solubilizer/Humectant | 10.0 |
| Denatured Ethanol SD#40 | Solvent | 10.0 |
| Polysorbate-20 (Tween-20) | Emulsifier | 2.0 |
| Hemp oil, 10% CBD | Pain Relief | 5.0 |

Water is added to magnesium chloride salt and mixed to form a clear solution. In a separate container, propylene glycol, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing. A white lotion is formed.

Example 3C

Compositions for Topical Administration

Spray on composition is prepared using the ingredients listed in Table 7.

TABLE 7

| Ingredient | Function | Amount (weight percent) |
|---|---|---|
| Water | Aqueous solvent | 35.0 |
| Magnesium Chloride Hexahydrate | Pain relief/ muscle relaxation | 34.0 |
| Menthol | Pain Relief | 2.0 |
| Methyl Salicylate | Pain Relief | 10.0 |
| Camphor | Pain Relief | 2.0 |
| Denatured Ethanol SD#40 | Solvent | 10.0 |
| Polysorbate-20 (Tween-20) | Emulsifier | 2.0 |
| Hemp oil, 10% CBD | Pain Relief | 5.0 |

Water is added to magnesium chloride salt and mixed to form a clear solution. In a separate container, menthol, camphor, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing. A white lotion is formed.

Example 3D

Compositions for Topical Administration

Spray on composition is prepared using the ingredients listed in Table 8.

TABLE 8

| Ingredient | Function | Amount (weight percent) |
|---|---|---|
| Water | Aqueous solvent | 26.0 |
| Magnesium Chloride Hexahydrate | Pain relief/ muscle relaxation | 45.0 |
| Menthol | Pain Relief | 2.0 |
| Methyl Salicylate | Pain Relief | 10.0 |
| Denatured Ethanol SD#40 | Solvent | 10.0 |
| Polysorbate-20 (Tween-20) | Emulsifier | 2.0 |
| Hemp oil, 10% CBD | Pain Relief | 5.0 |

Water is added to magnesium chloride salt and mixed to form a clear solution. In a separate container, menthol, methyl salicylate and ethanol are mixed until dissolution. The alcoholic phase and aqueous phases are combined. Then, in a separate vessel, hemp oil is mixed with Polysorbate-20, and then added to the combined alcoholic and aqueous phase while mixing. A white lotion is formed.

Example 3E

Compositions for Topical Administration

Spray on composition is prepared using the ingredients listed in Table 9.

TABLE 9

| Ingredient | Function | Amount (weight percent) |
|---|---|---|
| Water | Aqueous solvent | 37.0 |
| Magnesium Chloride Hexahydrate | Pain relief/ muscle relaxation | 34.0 |
| Menthol | Pain Relief | 2.0 |
| Methyl Salicylate | Pain Relief | 10.0 |
| Denatured Ethanol SD#40 | Solvent | 10.0 |
| Solubilisant LRI | Emulsifier/Solvent | 2.0 |
| Hemp oil, 10% CBD | Pain Relief | 5.0 |

Solubisant LRI is an excipient provided by Sensient Cosmetic Technologies and containing PPG-26-Buteth-26 (and) PEG-40 Hydrogenated Castor Oil (and) Water.

Water is added to magnesium chloride salt and mixed to form a clear solution. In a separate container, menthol, methyl salicylate and ethanol are mixed until dissolution. The alcoholic phase and aqueous phases are combined. Then, in a separate vessel, hemp oil is mixed with Solubilisant LRI, and then added to the combined alcoholic and aqueous phase while mixing. A white lotion is formed.

Example 3F

Compositions for Topical Administration

Spray on composition is prepared using the ingredients listed in Table 10.

TABLE 10

| Ingredient | Function | Amount (weight percent) |
|---|---|---|
| Water | Aqueous solvent | 36.70 |
| Allantoin | Anti allergic | 0.20 |
| Magnesium Chloride Hexahydrate | Pain Relief | 34.0 |
| Menthol | Pain Relief | 2.0 |
| Methyl Salicylate | Pain Relief | 10.0 |
| Bisabolol | Soothing agent | 0.10 |
| Denatured Ethanol SD#40 | Solvent | 10.0 |
| Solubilisant LRI | Solubilizer | 2.0 |
| Hemp oil, 10% CBD | Pain Relief | 5.0 |

Water is added to Allantoin, and mixed. Then magnesium chloride salt is added and mixed to form a clear solution. In a separate container, menthol, methyl salicylate, bisabolol, and ethanol are mixed until dissolution. The alcoholic phase and aqueous phases are combined. Then, in a separate vessel, hemp oil is mixed with Solubilisant LRI, and then added to the combined alcoholic and aqueous phase while mixing. A white lotion is formed.

In examples 3A-3F, a spray-on, pain relieving composition is prepared. The amount of CBD in the composition is between 0.45 and 0.55 g per 100 g of composition. The composition formed is a white lotion, having a viscosity of 100 cps or less. The composition can be applied to a patient in need of pain relief by spraying for example, from a spray bottle onto skin. The phases of the composition may separate over time. In order to make sure that the composition is sprayed in a uniform fashion, the spray bottle may contain instructions to direct the user to shake the bottle before spraying onto the skin.

The compositions described in examples 3A-3F have been found to be free of sediments and free of salt crystals. When sprayed on the skin, the drops are small and uniformly spread. The compositions are not sticky, and dry quickly when applied to the skin. They have been found to be useful by athletes and others who perform outdoor activities. The compositions are also advantageous in that they do not leave an oily residue on the skin, and are easily applied to areas of the skin.

Example 4A

Preparation of Cream Comprising CBD and Magnesium Chloride

A cream based on an oil in water emulsion was prepared according to the ingredients in Table 11.

TABLE 11

| Ingredient | Function | Amount (weight percent) |
|---|---|---|
| Water | Aqueous solvent | 35.90 |
| Magnesium Chloride Hexahydrate | Pain Relief | 22.0 |
| Caprylic/Capric Triglyceride | Emollient | 5.0 |
| C12-C15 alkyl benzoate | Emollient | 3.0 |
| Cyclopentasiloxane | Lubricant | 4.0 |
| Vitamin E acetate | Anti Oxidant | 0.10 |
| Bisabolol | Soothing agent | 0.10 |
| Hemp oil - Sativa (Cannabis) Seed oil | Carrier Oil | 1.00 |
| CBD (>97% isolate) | Pain Relief | 1.00 |
| Phenoxyethanol | Preservative | 0.9 |
| Ethylhexylglycerin | Preservative | 0.2 |
| Polyacrylate Crosspolymer- | stabilizing and | 1.00 |

TABLE 11-continued

| Ingredient | Function | Amount (weight percent) |
|---|---|---|
| 6 | texturizing polymer | |
| Caesalpinia Spinosa Gum | Thickening | 0.80 |
| Methyl Salicylate | Pain relief | 15.00 |
| Menthol | Cooling and pain relief | 10.00 |
| Polysorbate-20 | | As needed |

Magnesium chloride was dissolved in water and heated. In a separate vessel, the oily phase was heated. Polyacrylate crosspolymer-6 and Caesalpinia Spinosa Gum was added and homogenize until a lotion-like consistency was obtained. The oily phase was added to the water phase and homogenized vigorously for 5 minutes, then cooled.

In a separate container, menthol and methyl salicylate were heated and mixed until dissolution, then added to the emulsion. Polysorbate-20 was added dropwise as necessary to modify the cream texture. A cream with a viscosity of greater than 50,000 cps was formed.

Example 4B

A cream composition as oil in water emulsion comprising CBD and THC as active ingredients was prepared using the ingredients listed in Table 12:

TABLE 12

| Ingredient | Function | Amount (weight percent) |
|---|---|---|
| Water | Aqueous solvent | 24.55 |
| Propylene Glycol | Solvent | 10.0 |
| Menthol | Pain Relief | 3.0 |
| Camphor | Pain Relief | 4.0 |
| Caprylic/Capric Trigylceride | Emollient | 10.00 |
| C12-C15 Alkyl Benzoate | Emollient | 5.00 |
| Cyclopentasiloxane | Lubricant | 5.00 |
| Vitamin E Acetate | Anti Oxidant | 0.10 |
| Bisabolol | Soothing Agent | 0.10 |
| BHT | Anti Oxidant | 0.05 |
| THC (tetrahydrocannabiniol) as 25% in medium chain triglyceride (MCT) oil | Pain Relief | 1.00 |
| CBD as 18% in MCT Oil | Pain Relief | 1.40 |
| Phenoxyethanol and Ethylhexylglycerin | Preservative | 1.00 |
| Polyacrylate Crosspolymer-6 | stabilizing and texturizing polymer | 0.80 |
| C14-C122 Alcohols and C12-20 Alkyl Glucoside | Emulsifier | 3.00 |
| Water | Aqueous solvent | 15.00 |
| Magnesium Chloride | Pain Relief/muscle relaxation | 15.00 |
| Hydroxyethyl Acrylate/Sodium Acryloyldimethyl Taurate Copolymer | Stabilizing polymer | 1.00 |

Menthol in crystalline form and camphor are added to the propylene glycol and heated until dissolved then added to the first part of water which is heated while mixing. In a separate vessel, the oily phase ingredients (caprylic/capric triglyceride until C14-C122 Alcohols and C12-20 Alkyl Glucoside) are mixed and heated. The oily phase is mixed with the main vessel and homogenized while heating, then cooled. The remainder of the water is heated in a separate vessel with magnesium chloride until complete dissolution.

The magnesium chloride solution is then added to the main vessel and homogenized while heating. Hydroxyethyl Acrylate/Sodium Acryloyldimethyl Taurate Copolymer is then added to the main vessel and homogenized, while cooling.

A cream is formed having 0.25% weight percentage CBD and 0.25% weight percentage THC as well as menthol and camphor, and magnesium salt in a high concentration.

Example 4C

A cream composition (oil in water emulsion) comprising CBD as active ingredients was prepared using the ingredients listed in Table 13:

TABLE 13

| Ingredient | Function | Amount (weight percent) |
|---|---|---|
| Water | Aqueous solvent | 25.28 |
| Propylene Glycol | Solvent | 10.0 |
| Menthol | Pain Relief | 3.0 |
| Camphor | Pain Relief | 4.0 |
| Caprylic/Capric Trigylceride | Emollient | 10.00 |
| C12-C15 Alkyl Benzoate | Emollient | 5.00 |
| Cyclopentasiloxane | Lubricant | 5.00 |
| Vitamin E Acetate | Anti Oxidant | 0.10 |
| Bisabolol | Soothing Agent | 0.10 |
| BHT | Anti Oxidant | 0.05 |
| Hemp oil - Sativa (Cannabis) Seed oil | Carrier Oil | 1.00 |
| CBD (>97% isolate) | Pain Relief | 0.67 |
| Phenoxyethanol and Ethylhexylglycerin | Preservative | 1.00 |
| Polyacrylate Crosspolymer-6 | stabilizing and texturizing polymer | 0.80 |
| C14-C122 Alcohols and C12-20 Alkyl Glucoside | Emulsifier | 3.00 |
| Water | Aqueous solvent | 15.00 |
| Magnesium Chloride | Pain Relief/muscle relaxation | 15.00 |
| Hydroxyethyl Acrylate/Sodium Acryloyldimethyl Taurate Copolymer | Stabilizing polymer | 1.00 |

Menthol in crystalline form and camphor are added to the propylene glycol and heated until dissolved then added to the first part of water which is heated while mixing. In a separate vessel, the oily phase ingredients (caprylic/capric triglyceride until C14-C122 Alcohols and C12-20 Alkyl Glucoside) are mixed and heated. The oily phase is mixed with the main vessel and homogenized while heating, then cooled. The remainder of the water is heated in a separate vessel with magnesium chloride until complete dissolution. The magnesium chloride solution is then added to the main vessel and homogenized while heating. Hydroxyethyl Acrylate/Sodium Acryloyldimethyl Taurate Copolymer is then added to the main vessel and homogenized, while cooling.

A cream is formed having 0.67% weight percent CBD as well as menthol and camphor, and magnesium salt in a high concentration.

Example 4D

CBD Cream with Magnesium Sulfate

A cream based on oil in water emulsion was prepared according to the ingredients in Table 14.

TABLE 14

| Ingredient | Function | Amount (weight percent) |
|---|---|---|
| Water | Aqueous solvent | 35.90 |
| Magnesium Sulfate-Heptahydrate | Pain Relief | 22.0 |
| Caprylic/Capric Triglyceride | Emollient | 5.0 |
| C12-C15 alkyl benzoate | Emollient | 3.0 |
| Cyclopentasiloxane | Lubricant | 4.0 |
| Vitamin E acetate | Anti Oxidant | 0.10 |
| Bisabolol | Soothing agent | 0.10 |
| Hemp oil - Sativa (Cannabis) Seed oil | Carrier Oil | 1.00 |
| CBD (>97% isolate) | Pain Relief | 1.00 |
| Phenoxyethanol | Preservative | 0.9 |
| Ethylhexylglycerin | Preservative | 0.2 |
| Polyacrylate Crosspolymer-6 | stabilizing and texturizing polymer | 1.00 |
| Caesalpinia Spinosa Gum | Thickener | 0.80 |
| Methyl Salicylate | Pain relief | 15.00 |
| Menthol | Cooling and pain relief | 10.00 |
| Polysorbate-20 | | As needed |

Magnesium chloride was dissolved in water and heated. In a separate vessel, the oily phase (Caprylic/Capric Triglyceride and next 8 ingredients) was heated. Polyacrylate crosspolymer-6 and Caesalpinia Spinosa Gum was added to the oily phase and homogenized until a lotion-like consistency was obtained. The oily phase was added to the water phase and homogenized vigorously for 5 minutes, then cooled.

In a separate container, menthol and methyl salicylate were heated and mixed until dissolution, then added to the emulsion. Polysorbate-20 was added dropwise as necessary to modify the cream texture. A cream with a viscosity of greater than 50,000 cps was formed.

The creams described above allow for high concentrations of magnesium salts, such as sulfate and chloride, to provide pain relief, while including other pain relieving agents such as menthol and camphor. These creams provide emulsions, which allow for concentrations of cannabinoids such as CBD and THC in concentrations ranging from 0.25% to about 2.5% weight percentage cannabinoid.

The oil in water emulsions described in examples 4A to 4D were not stable and found to be separated following stability tests under accelerated conditions. It is possible that changing the above thickeners and surfactants might help solve the problem, Currently, loading high electrolyte content did not lead to stable compositions in attempts made to formulate oil in water creams.

Example 5A

CBD Roll-On with Magnesium Sulfate

A roll-on composition is prepared according to the ingredients in Table 15.

TABLE 15

| Ingredient | Function | Amount (weight percent) |
|---|---|---|
| Water | Aqueous solvent | 38.55 |
| Magnesium Sulfate Heptahydrate | Pain Relief | 18.5 |
| Propylene Glycol | Solvent | 10.00 |
| Menthol | Pain Relief | 3.00 |
| Camphor | Pain Relief | 4.00 |
| Cetyl PEG/PPG-10/1 Dimethicone | Emulsifier | 2.50 |
| Ethylhexyl palmitate | Emollient | 7.90 |
| Beeswax | Thickener | 0.50 |
| Hydrogenated castor oil | Emulsifier | 0.50 |
| Cyclopentasiloxane | Lubricant | 8.00 |
| BHT | Anti Oxidant | 0.05 |
| Bisabolol | Soothing agent | 0.10 |
| Hemp oil - Sativa (Cannabis) Seed oil | Carrier Oil | 1.00 |
| Cannabidiol | Pain relief | 0.40 |

Water and Magnesium sulfate are mixed until completely dissolved. Menthol and camphor are combined with propylene glycol and mixed until complete dissolved. Analgesic phase is added to the water phase while stirring. The next seven ingredients (oily phase) are mixed in a separate container and heated until solids are dissolved. In a separate vessel CBD is dissolved in hemp oil, and added into the oily phase. The water phase is added slowly while heating into the oily phase, then homogenized until a desired viscosity is obtained.

Example 5B

CBD Roll-On with Magnesium Sulfate

A roll-on composition was prepared according to the ingredients in Table 16.

TABLE 16

| Ingredient | Function | Amount (weight percent) |
|---|---|---|
| Water | Aqueous solvent | 31.30 |
| Magnesium Sulfate Heptahydrate | Pain Relief | 25.00 |
| Menthol | Pain Relief | 10.00 |
| Methyl Salicylate | Pain Relief | 15.00 |
| Cetyl PEG/PPG-10/1 Dimethicone | Emulsifier | 3.00 |
| Cyclopentasiloxane | Lubricant | 14.00 |
| Bisabolol | Soothing agent | 0.10 |
| Hemp oil - Sativa (Cannabis) Seed oil | Carrier Oil | 1.00 |
| Cannabidiol | Pain relief | 0.60 |

Water and Magnesium sulfate are mixed until completely dissolved. Menthol is mixed with methyl salicylate until complete dissolved. Analgesic phase is added to the water phase while stirring. The next three ingredients (oily phase) are mixed in a separate container and mixed until a homogenous liquid is obtained. In a separate vessel CBD is dissolved in hemp oil, and added into the oily phase. The water phase is added slowly while heating into the oily phase, then homogenized until a desired viscosity is obtained.

The formulations in these examples indicate that water in oil emulsions can be formed, having high magnesium content while maintaining long-term stability.

Example 6A

CBD Spray-On with Magnesium Sulfate

A spray-on composition is prepared according to the ingredients in Table 17. The composition was prepared so that an aqueous and oily phase would separate, and a user would shake before use to combine the phases, then spray upon the affected area. After shaking and applying, when the bottle containing the composition is allowed to rest, the phases separate.

TABLE 17

| Ingredient | Function | Amount (weight percent) |
|---|---|---|
| Water | Aqueous solvent | 37.20 |
| Magnesium Sulfate Heptahydrate | Pain Relief | 34.00 |
| Menthol | Pain Relief | 3.00 |
| Camphor | Pain Relief | 4.00 |
| BHT | Preservative | 0.05 |
| Propylene Glycol | Solvent, Humectant | 5.00 |
| Ethanol (99%) | Solvent | 10.00 |
| Polysorbate-20 | Emulsifier | 2.00 |
| Hemp oil - Sativa (Cannabis) Seed oil | Carrier Oil | 4.50 |
| Cannabidiol | Pain relief | 0.25 |

Water and Magnesium sulfate are mixed until completely dissolved. In a separate vessel, menthol is mixed with ethanol, propylene glycol, BHT and camphor and heated until completely dissolved. The solutions are combined in a main vessel. In a separate vessel CBD is dissolved in hemp oil, and added into the main vessel. A homogenous white lotion is obtained, which separates shortly into two phases, which can be recombined into a lotion by shaking.

Example 6B

CBD Spray-On with Magnesium Sulfate

A spray-on composition is prepared according to the ingredients in Table 18. The composition was prepared so that an aqueous and oily phase would separate, and a user would shake before use to combine the phases, then spray upon the affected area. After shaking and applying, when the bottle containing the composition is allowed to rest, the phases separate.

TABLE 18

| Ingredient | Function | Amount (weight percent) |
|---|---|---|
| Water | Aqueous solvent | 33.50 |
| Magnesium Sulfate Heptahydrate | Pain Relief | 34.00 |
| Menthol | Pain Relief | 10.00 |
| Methyl Salicylate | Pain Relief | 15.00 |
| Polysorbate-20 | Emulsifier | 2.00 |
| Hemp seed oil | Carrier | 4.25 |
| Cannabidiol | Pain relief | 0.25 |
| Phenoxyethanol & Ethylhexylglycerin | Preservative | 1.00 |

Water and Magnesium sulfate are mixed until completely dissolved. In a separate vessel, menthol is mixed with methyl salicylate until completely dissolved. The analgesic phase is added to the main vessel. In a separate vessel, Polysorbate 20, CBD, hemp oil, and Phenoxyethanol & Ethylhexylglycerin are mixed and heated until completely dissolved. The oil solution is then added into the main vessel to form a low viscous milk-like liquid. The formulation was stable for 12 months.

Example 7A: Two Phase Compositions

The following examples (7A-7J) are of two-phase compositions which are formulated for pain relief. They are made using processes similar to those described in examples 6A and 6B. These are intended to be shaken before application, to combine the phases. Various cannabinoids are used, from different sources, in various amounts. A two-phase composition was prepared using the ingredients in Table 19, and was found to be stable for 12 months.

TABLE 19

| Ingredient | Function | Amount (weight percent) |
|---|---|---|
| Water | Aqueous solvent | 37.2 |
| Magnesium Chloride Hexahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Hemp-Derived CBD Isolate > 97% | Pain Relief | 0.25 |
| Hemp oil - Sativa (Cannabis) Seed oil | Carrier Oil | 4.5 |

Example 7B: Two Phase Compositions

A two-phase composition is prepared using the ingredients in Table 20.

TABLE 20

| Ingredient | Function | Amount (weight percent) |
|---|---|---|
| Water | Aqueous solvent | 35.95 |
| Magnesium Chloride Hexahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Hemp-Derived CBD Isolate > 97% | Pain Relief | 1.5 |
| Hemp oil - Sativa (Cannabis) Seed oil | Carrier Oil | 4.5 |

Example 7C: Two Phase Compositions

A two-phase composition is prepared using the ingredients in Table 21.

In the composition, magnesium sulfate is used for pain relief/muscle relaxation.

TABLE 21

| Ingredient | Function | Amount (weight percent) |
|---|---|---|
| Water | Aqueous solvent | 37.2 |
| Magnesium Sulfate Heptahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Hemp-Derived CBD Isolate > 97% | Pain Relief | 0.25 |
| Hemp oil - Sativa (Cannabis) Seed oil | Carrier Oil | 4.5 |

Example 7D: Two Phase Compositions

A two-phase composition is prepared using the ingredients in Table 22.

In the composition, magnesium sulfate is used for pain relief/muscle relaxation.

TABLE 22

| Ingredient | Function | Amount (weight percent) |
|---|---|---|
| Water | Aqueous solvent | 35.95 |
| Magnesium Sulfate Heptahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Hemp-Derived CBD Isolate > 97% | Pain Relief | 1.5 |
| Hemp oil - Sativa (Cannabis) Seed oil | Carrier Oil | 4.5 |

Example 7E: Two Phase Compositions

A two-phase composition is prepared using the ingredients in Table 23.

In the composition, both CBD and THC were used from a pre-mixed oil (10% of each cannabinoid) and used, in an amount of 2.5% weight percentage. The final total amount of CBD and THC was 0.5% weight percentage.

TABLE 23

| Ingredient | Function | Amount (weight percent) |
|---|---|---|
| Water | Aqueous solvent | 39.45 |
| Magnesium Chloride Hexahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| CANNABIS OIL (10% $\Delta^9$THC, 10% CBD, CBN < 1.5% ) | Pain Relief | 2.5 |

Example 7F: Two Phase Compositions

A two-phase composition is prepared using the ingredients in Table 24.

In the composition, both CBD and THC were used, from different sources, in a total amount of 0.25% weight percentage.

TABLE 24

| Ingredient | Function | Amount (weight percent) |
|---|---|---|
| Water | Aqueous solvent | 36.94 |
| Magnesium Chloride Hexahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Cannabis derived distillate of $\Delta^9$THC or $\Delta^8$THC 90% | Pain Relief | 0.14 |

TABLE 24-continued

| Ingredient | Function | Amount (weight percent) |
|---|---|---|
| Hemp-Derived CBD Isolate > 97% | Pain Relief | 0.125 |
| Hemp oil - Sativa (Cannabis) Seed oil | Carrier Oil | 4.75 |

Example 7G: Two Phase Compositions

A two-phase composition is prepared using the ingredients in Table 25.

In the composition, both CBD and THC are used, from different sources, in a total amount of 1.5% weight percentage.

TABLE 25

| Ingredient | Function | Amount (weight percent) |
|---|---|---|
| Water | Aqueous solvent | 36.86 |
| Magnesium Chloride Hexahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Cannabis derived distillate of $\Delta^9$THC or $\Delta^8$THC 90% | Pain Relief | 0.84 |
| Hemp-Derived CBD Isolate > 97% | Pain Relief | 0.75 |
| Hemp oil - Sativa (Cannabis) Seed oil | Carrier Oil | 3.5 |

Example 7H: Two Phase Compositions

A two-phase composition is prepared using the ingredients in Table 26.

In the composition, both CBD and THC were derived from a pre-mixed oil (10% of each cannabinoid) and used, in an amount of 2.5% weight percentage. The final total amount of CBD and THC was 0.5% weight percentage. Magnesium sulfate is used for pain relief.

TABLE 26

| Ingredient | Function | Amount (weight percent) |
|---|---|---|
| Water | Aqueous solvent | 39.45 |
| Magnesium Sulfate Heptahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| CANNABIS OIL (10% $\Delta^9$THC, 10% CBD, CBN < 1.5%) | Pain Relief | 2.5 |

Example 71: Two Phase Compositions

A two-phase composition is prepared using the ingredients in Table 27.

In the composition, both CBD and THC are used, from different sources, in a total amount of 0.25% weight percentage. Magnesium sulfate is used for pain relief.

TABLE 27

| Ingredient | Function | Amount (weight percent) |
|---|---|---|
| Water | Aqueous solvent | 36.94 |
| Magnesium Sulfate Heptahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Cannabis derived distillate of $\Delta^9$THC or $\Delta^8$THC 90% | Pain Relief | 0.14 |
| Hemp-Derived CBD Isolate > 97% | Pain Relief | 0.125 |
| Hemp oil - Sativa (Cannabis) Seed oil | Carrier Oil | 4.75 |

Example 7J: Two Phase Compositions

A two-phase composition is prepared using the ingredients in Table 28.

In the composition, both CBD and THC are used, from different sources, in a total amount of 1.5% weight percentage. Magnesium sulfate is used for pain relief.

TABLE 28

| Ingredient | Function | Amount (weight percent) |
|---|---|---|
| Water | Aqueous solvent | 36.85 |
| Magnesium Sulfate Heptahydrate | Pain relief/muscle relaxation | 34.0 |
| Menthol | Pain Relief | 3.0 |
| Camphor | Pain Relief | 4.0 |
| BHT | Anti Oxidant | 0.05 |
| Propylene Glycol | Solvent, Humectant | 5.0 |
| Denatured Ethanol SD#40 | Solvent | 10.0 |
| Polysorbate-20 (Tween-20) | Emulsifier | 2.0 |
| Cannabis derived distillate of $\Delta^9$THC or $\Delta^8$THC 90% | Pain Relief | 0.85 |
| Hemp-Derived CBD Isolate > 97% | Pain Relief | 0.75 |
| Hemp oil - Sativa (Cannabis) Seed oil | Carrier Oil | 3.5 |

Example 8A: Water in Oil Compositions

The following examples (8A-8L) are of water in oil emulsions which are formulated for pain relief, and are prepared using the methods described in Examples 5A and 5B. These are intended to be administered in a roll-on container to the skin of a patient in need. Various cannabinoids are used, from different sources, in various amounts. These compositions are expected to be to be stable for more than 12 months. A water in oil emulsion for pain relief, adapted to be administered in a roll-on form is prepared using the ingredients in Table 29.

In the formulation, 0.4% weight percentage CBD was introduced, and the composition was found to be stable for more than 12 months.

TABLE 29

| Ingredient | Function | Amount (weight percent) |
|---|---|---|
| Water | Aqueous solvent | 38.55 |
| Magnesium Chloride Hexahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Hemp oil | Solvent for CBD | 1.0 |
| CBD > 97% Isolate | Pain Relief | 0.4 |

Example 8B: Water in Oil Roll-on Composition

A water in oil emulsion for pain relief, adapted to be administered in a roll-on form is prepared using the ingredients in Table 30.

In the formulation, 0.25% weight percentage CBD is introduced.

TABLE 30

| Ingredient | Function | Amount (weight percent) |
|---|---|---|
| Water | Aqueous solvent | 38.55 |
| Magnesium Chloride Hexahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Hemp oil - Sativa (Cannabis) Seed oil | Carrier Oil | 1.15 |
| CBD > 97% Isolate | Pain Relief | 0.25 |

Example 8C: Water in Oil Roll-on Composition

A water in oil emulsion for pain relief, adapted to be administered in a roll-on form is prepared using the ingredients in Table 31.

In the formulation, 1.5% weight percentage CBD is introduced.

TABLE 31

| Ingredient | Function | Amount (weight percent) |
|---|---|---|
| Water | Aqueous solvent | 36.95 |
| Magnesium Chloride Hexahydrate | Pain relief/muscle relaxation | 18.5 |
| Propylene Glycol | Solvent | 15.0 |

TABLE 31-continued

| Ingredient | Function | Amount (weight percent) |
|---|---|---|
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Hemp oil - Sativa (Cannabis) Seed oil | Carrier Oil | 1.5 |
| CBD > 97% Isolate | Pain Relief | 1.5 |

Example 8D: Water in Oil Roll-on Composition

A water in oil emulsion for pain relief, adapted to be administered in a roll-on form is prepared using the ingredients in Table 32.

In the formulation, 0.4% weight percentage CBD was used with magnesium sulfate.

TABLE 32

| Ingredient | Function | Amount (weight percent) |
|---|---|---|
| Water | Aqueous solvent | 38.55 |
| Magnesium Sulfate Heptahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Hemp oil | Solvent for CBD | 1.0 |
| CBD > 97% Isolate | Pain Relief | 0.4 |

Example 8E: Water in Oil Roll-on Composition

A water in oil emulsion for pain relief, adapted to be administered in a roll-on form is prepared using the ingredients in Table 33.

In the formulation, 0.25% weight percentage CBD is used with magnesium sulfate.

TABLE 33

| Ingredient | Function | Amount (weight percent) |
|---|---|---|
| Water | Aqueous solvent | 38.55 |
| Magnesium Sulfate Heptahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Hemp oil - Sativa (Cannabis) Seed oil | Carrier Oil | 1.15 |
| CBD > 97% Isolate | Pain Relief | 0.25 |

Example 8F: Water in Oil Roll-on Composition

A water in oil emulsion for pain relief, adapted to be administered in a roll-on form is prepared using the ingredients in Table 34.

In the formulation, 1.5% weight percentage CBD is used with magnesium sulfate.

TABLE 34

| Ingredient | Function | Amount (weight percent) |
|---|---|---|
| Water | Aqueous solvent | 36.95 |
| Magnesium Sulfate Heptahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Hemp oil - Sativa (Cannabis) Seed oil | Carrier Oil | 1.5 |
| CBD > 97% Isolate | Pain Relief | 1.5 |

Example 8G: Water in Oil Roll-on Composition

A water in oil emulsion for pain relief, adapted to be administered in a roll-on form is prepared using the ingredients in Table 35.

In the formulation, both CBD and THC were derived from a pre-mixed oil (10% of each cannabinoid) and used, in an amount of 2.5% weight percentage. The final total amount of CBD and THC was 0.5% weight percentage. Magnesium Chloride is used for pain relief.

TABLE 35

| Ingredient | Function | Amount (weight percent) |
|---|---|---|
| Water | Aqueous solvent | 37.45 |
| Magnesium Chloride Hexahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 | Emulsifier | 2.5 |

TABLE 35-continued

| Ingredient | Function | Amount (weight percent) |
|---|---|---|
| Dimethicone | | |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cyclopentasiloxane | Light emollient, fast spreading | 8.0 |
| CANNABIS OIL (10% $\Delta^9$THC, 10% CBD, CBN < 1.5%) | Pain Relief | 2.5 |

Example 8H: Water in Oil Roll-on Composition

A water in oil emulsion for pain relief, adapted to be administered in a roll-on form is prepared using the ingredients in Table 36.

In the formulation, both CBD and THC are used, from different sources in a total amount of 0.25% weight percentage. Magnesium Chloride is used for pain relief.

TABLE 36

| Ingredient | Function | Amount (weight percent) |
|---|---|---|
| Water | Aqueous solvent | 37.55 |
| Magnesium Chloride Hexahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Cannabis derived distillate of $\Delta^9$THC or $\Delta^8$THC 90% | Pain Relief | 0.14 |
| Hemp-Derived CBD Isolate > 97% | Pain Relief | 0.125 |
| Hemp oil - Sativa (Cannabis) Seed oil | Carrier Oil | 2.135 |

Example 8L Water in Oil Roll-on Composition

A water in oil emulsion for pain relief, adapted to be administered in a roll-on form is prepared using the ingredients in Table 37.

In the formulation, both CBD and THC are used, from different sources in a total amount of 1.5% weight percentage. Magnesium Chloride is used for pain relief.

TABLE 37

| Ingredient | Function | Amount (weight percent) |
|---|---|---|
| Water | Aqueous solvent | 37.55 |
| Magnesium Chloride Hexahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cyclopentasiloxane | Light emollient, fast spreading | 8.0 |
| Cannabis derived distillate of $\Delta^9$THC or $\Delta^8$THC 90% | Pain Relief | 0.84 |
| Hemp-Derived CBD Isolate > 97% | Pain Relief | 0.75 |
| Hemp oil - Sativa (Cannabis) Seed oil | Carrier Oil | 0.81 |

Example 8J: Water in Oil Roll-on Composition

A water in oil emulsion for pain relief, adapted to be administered in a roll-on form is prepared using the ingredients in Table 38.

In the formulation, both CBD and THC were derived from a pre-mixed oil (10% of each cannabinoid) and used, in an amount of 2.5% weight percentage. The final total amount of CBD and THC was 0.5% weight percentage.

TABLE 38

| Ingredient | Function | Amount (weight percent) |
|---|---|---|
| Water | Aqueous solvent | 37.45 |
| Magnesium Sulfate Heptahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cyclopentasiloxane | Light emollient, fast spreading | 8.0 |
| CANNABIS OIL (10% $\Delta^9$THC, 10% CBD, CBN < 1.5%) | Pain Relief | 2.5 |

Example 8K: Water in Oil Roll-on Composition

A water in oil emulsion for pain relief, adapted to be administered in a roll-on form is prepared using the ingredients in Table 39.

In the formulation, both CBD and THC are used, from different sources in a total amount of 0.25% weight percentage. Magnesium Sulfate is used for pain relief.

TABLE 39

| Ingredient | Function | Amount (weight percent) |
|---|---|---|
| Water | Aqueous solvent | 37.55 |
| Magnesium Sulfate Heptahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Cannabis derived distillate of $\Delta^9$THC or $\Delta^8$THC 90% | Pain Relief | 0.14 |
| Hemp-Derived CBD Isolate > 97% | Pain Relief | 0.125 |
| Hemp oil - Sativa (Cannabis) Seed oil | Carrier Oil | 2.135 |

Example 8L: Water in Oil Roll-on Composition

A water in oil emulsion for pain relief, adapted to be administered in a roll-on form is prepared using the ingredients in Table 40.

In the formulation, both CBD and THC are used, from different sources in a total amount of 1.5% weight percentage. Magnesium Sulfate is used for pain relief.

TABLE 40

| Ingredient | Function | Amount (weight percent) |
|---|---|---|
| Water | Aqueous solvent | 37.55 |
| Magnesium Sulfate Heptahydrate | Pain relief/muscle relaxation | 18.5 |
| Propylene Glycol | Solvent | 15.0 |
| Camphor | Pain Relief | 4.0 |
| Menthol | Pain Relief | 3.0 |
| ABIL EM 90 Cetyl PEG/PPG-10/1 Dimethicone | Emulsifier | 2.5 |
| Ethylhexyl Palmitate | Emollient | 7.9 |
| Beeswax | Thickener | 0.5 |
| HYDROGENATED CASTOR OIL | Thickener | 0.5 |
| BHT | Anti Oxidant | 0.05 |
| Bisabolol | Soothing agent | 0.1 |
| Cylopentasiloxane | Light emollient, fast spreading | 8.0 |
| Cannabis derived distillate of $\Delta^9$THC or $\Delta^8$THC 90% | Pain Relief | 0.84 |
| Hemp-Derived CBD Isolate > 97% | Pain Relief | 0.75 |
| Hemp oil - Sativa (Cannabis) Seed oil | Carrier Oil | 0.8 |

An embodiment of the invention relates to a topical pharmaceutical composition comprising a magnesium salt, a cannabinoid and at least one additional topical analgesic agent. Optionally, the at least one additional topical analgesic agent is selected from the group consisting of: alcohol, ethoxylated alkyl alcohol, allantoin, allyl isothiocyanate, aluminum acetate, aluminum chloride hexahydrate, aluminum hydroxide, ammonia solution, aspirin, benzalkonium chloride, benzethonium chloride, benzocaine, benzyl alcohol, bismuth sodium tartrate, bithionol, butamben picrate, calamine, camphor, camphorated metacresol, capsaicin, capsicum, capsicum oleoresin, cetalkonium chloride, chloral hydrate, chlorobutanol, chlorpheniramine maleate, creosote, cupric sulfate, cyclomethycaine sulfate, dexpanthenol, dibucaine, dimethisoquin hydrochloride, diperodon hydrochloride, diphenhydramine hydrochloride, dyclonine hydrochloride, ephedrine hydrochloride, ergot fluid extract, eucalyptus oil, eugenol, ferric chloride, glycerin, glycol salicylate, hectorite, hexylresorcinol, histamine dihydrochloride, hydrocortisone, hydrocortisone acetate, hydrogen peroxide, impatiens biflora tincture, iron oxide, isopropyl alcohol, juniper tar, lanolin, lidocaine, menthol, merbromin, methapyrilene hydrochloride, methyl nicotinate, methyl salicylate, panthenol, parethoxycaine hydrochloride, pectin, peppermint oil, phenol, phenolate sodium, phenyltoloxamine dihydrogen citrate, povidone-vinylacetate copolymers, pramoxine hydrochloride, pyrilamine maleate, resorcinol, salicylamide, simethicone, sodium bicarbonate, sodium borate, sulfur, tannic acid, tetracaine, thymol, topical starch, tripelennamine hydrochloride, trolamine, trolamine salicylate (trietnanolamine salicylate), turpentine oil, zinc acetate, zinc oxide, zinc sulfate, zirconium oxide and zyloxin. Optionally, the additional topical analgesic agent is selected from the group consisting of: methyl salicylate, menthol and camphor. Optionally, the composition comprises methyl salicylate and menthol. Optionally, the cannabinoid is Optionally, the cannabinoid is present in an amount between about 0.1% and about 10% weight percent of the composition. Optionally, the cannabinoid is present in an amount between about 0.1% and about 2% weight percent of the composition. Optionally, the cannabinoid is present in an amount of about 0.5% weight percent of the composition. Optionally, the methyl salicylate is present in an amount between about 0.1% and about 30% weight percent of the composition. Optionally, the methyl salicylate is present in an amount between about 10% and about 20% weight percent of the composition. Optionally, the methyl salicylate is present in an amount of about 15% weight percent of the composition. Optionally, the methyl salicylate is present in an amount of about 10% weight percent of the composition. Optionally, magnesium ion in the composition is present in an amount between about 0.025% and about 16% weight percent of the composition. Optionally, magnesium ion in the composition is present in an amount between 0.25% and 9% weight percent of the composition. Optionally, magnesium ion in the composition is present in an amount of about 1% to 7% weight percent of the composition. Optionally, magnesium ion in the composition is present in an amount of about 4% to 7% weight percent of the composition Optionally, the magnesium ion is added to the composition in the form of magnesium chloride, magnesium sulfate, magnesium bromide, magnesium carbonate, magnesium bicarbonate, magnesium hydroxide, magnesium oxide, magnesium L-pyrrolidone carboxylic acid, or hydrates thereof. Optionally, the magnesium ion is added to the composition in the form of magnesium chloride or a hydrate thereof. Optionally, the menthol is present in an amount between about 0.1% and about 15% weight percent of the composition. Optionally, the menthol is present in an amount between about 2% and about 15% weight percent of the composition. Optionally, the menthol is present in an amount of about 10% weight percent of the composition. Optionally, the menthol is present in an amount of about 3% weight percent of the composition. Optionally, the composition further comprises camphor. Optionally, camphor is present in an amount between about 0.1% and about 10% weight percent of the composition. Optionally, camphor is present in an amount between about 2% and about 5% weight percent of the composition. Optionally, the camphor is present in an amount of about 4% weight percent of the composition. Optionally, the composition is in the form of a spray, continuous spray, non-chlorofluorocarbon-based spray, aerosol foam, liquid, solution, powder, stick, roll-on, ointment, paste, or lotion. Optionally, the composition is in the form of a cream, wherein the viscosity is between 10,000 and 150,000 cps. Optionally, the composition is in the form of a spray, wherein the viscosity is between 10 and 1,000 cps. Optionally, the composition is in the form of a roll-on, wherein the viscosity is between 800 and 12,000 cps. Optionally, the composition further comprising an inert ingredient selected from the group consisting of: water, a solvent, an emulsifier, an emollient, a moisturizer, a pH adjustment agent, a polymer, a humectant, an occlusive agent, a preservative, a thickener, an anti-irritation agent, a conditioning agent, a buffer, a vitamin, an extract, a natural oil, a wax, a penetration enhancer, a peptide, a sugar derivative, a fatty acid, a fatty alcohol, a silicone, a poly-ethyl-glycol, a fragrance, a pigment, an ester, a triglyceride and an absorbing powder. Optionally, the composition is in the form of an emulsion. Optionally, the pH of the composition is between 5.5 and 7.0. Optionally, the cannabinoid is CBD and the composition has less than 10 mg/g of THC. Optionally, the composition is free of THC. Optionally, the emulsion remains stable for at least three months at 40° C. and 75% relative humidity. Optionally, the composition further comprises at least 10% propylene glycol. Optionally, the compositions further comprise cyclopentasiloxane. Optionally, the amount of cyclopentasiloxane is in an amount of between 5-15%. Optionally, the composition further comprising between 5-20% ethyl alcohol.

Some embodiments relate to a kit comprising a composition as described above, and instructions, wherein the composition is a biphasic composition comprising an oil phase and an aqueous phase and the composition is enclosed in a container, and wherein the instructions instruct to shake the container before administration of the composition.

Some embodiments relate to a method for treatment of pain comprising topically administering to a patient in need thereof, a composition described above. Optionally, the pain is pain and/or itching associated with minor burns, sunburn, minor cuts, scrapes, insect bites or minor skin irritations, muscle pain, joint pain, backache, arthritis, strains, bruises, back pain, neck pain, knee pain, foot pain, or sprains. Optionally, the composition is administered in an amount of between 0.1 ml and 10.0 ml per application. Optionally, the composition is administered between once and 4 times daily. Optionally, the patient shakes the composition before administration.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A topical pharmaceutical composition comprising magnesium chloride, a cannabinoid selected from the group consisting of cannabidiol (CBD) and tetrahydrocannabinol (THC), an emulsifier and at least one additional topical analgesic agent, selected from the group consisting of methyl salicylate, menthol and camphor; wherein the magnesium ion in the composition is present in an amount of 1% to 6% of the composition and wherein the cannabinoid is present in an amount between 0.25% and 1.5% of the composition, and wherein the composition is a water-in-oil emulsion.

2. The composition according to claim 1, comprising both CBD and THC.

3. The composition according to claim 1, wherein magnesium ion in the composition is present in an amount of 4% to 6% of the composition.

4. The composition according to claim 1 in the form of a cream, spray, continuous spray, non-chlorofluorocarbon-based spray, aerosol foam, liquid, solution, powder, stick, roll-on, ointment, paste, or lotion.

5. The composition according to claim 4 in the form of a cream, wherein the viscosity is between 10,000 and 150,000 cps.

6. The composition according to claim 4 in the form of a spray, wherein the viscosity is between 10 and 1,000 cps.

7. The composition according to claim 4 in the form of a roll-on, wherein the viscosity is between 800 and 12,000 cps.

8. The composition according to claim 5, wherein the cannabinoid is present in an amount of 0.5% by weight of the composition.

* * * * *